US009040086B2

(12) United States Patent
Percel et al.

(10) Patent No.: US 9,040,086 B2
(45) Date of Patent: *May 26, 2015

(54) TIMED, SUSTAINED RELEASE SYSTEMS FOR PROPRANOLOL

(75) Inventors: Phillip J. Percel, Troy, OH (US); Krishna S. Vishnupad, Dayton, OH (US); Gopi M. Venkatesh, Vandalia, OH (US)

(73) Assignee: Aptalis Pharmatech, Inc., Vandalia, OH (US)

( * ) Notice: Subject to any disclaimer, the term of this patent is extended or adjusted under 35 U.S.C. 154(b) by 1564 days.

This patent is subject to a terminal disclaimer.

(21) Appl. No.: 11/500,892

(22) Filed: Aug. 9, 2006

(65) Prior Publication Data

US 2006/0269607 A1  Nov. 30, 2006

Related U.S. Application Data

(63) Continuation of application No. 10/453,848, filed on Jun. 2, 2003, which is a continuation-in-part of application No. 10/334,052, filed on Dec. 30, 2002, now abandoned, which is a continuation of application No. 09/971,167, filed on Oct. 4, 2001, now Pat. No. 6,500,454.

(51) Int. Cl.
*A61K 9/16* (2006.01)
*A61K 9/50* (2006.01)
*A61K 31/138* (2006.01)

(52) U.S. Cl.
CPC ............. *A61K 9/5084* (2013.01); *A61K 9/5078* (2013.01); *A61K 31/138* (2013.01)

(58) Field of Classification Search
None
See application file for complete search history.

(56) References Cited

U.S. PATENT DOCUMENTS

| | | |
|---|---|---|
| 3,184,386 A | 5/1965 | Stephenson |
| 3,558,768 A | 1/1971 | Klippel |
| 3,885,026 A | 5/1975 | Heinemann et al. |
| 4,078,051 A | 3/1978 | Pomot et al. |
| 4,138,475 A | 2/1979 | McAnish et al. |
| 4,248,857 A | 2/1981 | DeNeale et al. |

(Continued)

FOREIGN PATENT DOCUMENTS

| | | |
|---|---|---|
| EP | 0052492 B1 | 2/1984 |
| EP | 0166440 A2 | 1/1986 |

(Continued)

OTHER PUBLICATIONS

"Low Substituted Hydroxypropylcellulose," Official Monographs for Part II, 2001, NRF, JP XIV, pp. 942-943.

(Continued)

*Primary Examiner* — Nissa Westerberg
(74) *Attorney, Agent, or Firm* — Cooley LLP

(57) ABSTRACT

A unit dosage form, such as a capsule or the like for delivering drugs into the body in a circadian release fashion, is comprising of one or more populations of propranolol-containing particles (beads, pellets, granules, etc.). Each bead population exhibits a pre-designed rapid or sustained release profile with or without a predetermined lag time of 3 to 5 hours. Such a circadian rhythm release cardiovascular drug delivery system is designed to provide a plasma concentration-time profile, which varies according to physiological need during the day, i.e., mimicking the circadian rhythm and severity/manifestation of a cardiovascular disease, predicted based on pharmaco-kinetic and pharmaco-dynamic considerations and in vitro/in vivo correlations.

19 Claims, 3 Drawing Sheets

Propranolol HCl TSR Formulations (Capsules): Release Profiles for Pilot and Pivotal Clinical Supplies

(56) References Cited

U.S. PATENT DOCUMENTS

| | | |
|---|---|---|
| 4,292,017 A | 9/1981 | Doepel |
| 4,305,502 A | 12/1981 | Gregory et al. |
| 4,369,172 A | 1/1983 | Schor et al. |
| 4,371,516 A | 2/1983 | Gregory et al. |
| 4,389,330 A | 6/1983 | Tice et al. |
| 4,389,393 A | 6/1983 | Schor et al. |
| 4,542,042 A | 9/1985 | Samejima et al. |
| 4,556,678 A | 12/1985 | Hsiao .................... 514/652 |
| 4,587,118 A | 5/1986 | Hsiao |
| 4,628,098 A | 12/1986 | Nohara et al. |
| 4,661,647 A | 4/1987 | Serpelloni et al. |
| 4,670,459 A | 6/1987 | Sjoerdsma |
| 4,689,333 A | 8/1987 | Nohara et al. |
| 4,698,101 A | 10/1987 | Koivurinta |
| 4,708,867 A | 11/1987 | Hsiao |
| 4,713,248 A | 12/1987 | Kjornaes et al. |
| 4,716,041 A | 12/1987 | Kjornaes et al. |
| 4,728,512 A | 3/1988 | Mehta et al. |
| 4,743,248 A | 5/1988 | Bartoo et al. |
| 4,752,470 A | 6/1988 | Mehta |
| 4,757,090 A | 7/1988 | Salpekar et al. |
| 4,760,093 A | 7/1988 | Blank et al. |
| 4,780,318 A | 10/1988 | Appelgren et al. |
| 4,786,508 A | 11/1988 | Ghebre-Sellassie et al. |
| 4,800,087 A | 1/1989 | Mehta |
| 4,803,213 A | 2/1989 | Iida et al. |
| 4,824,675 A | 4/1989 | Wong et al. |
| 4,832,880 A | 5/1989 | Staniforth |
| 4,840,799 A | 6/1989 | Appelgren et al. |
| 4,851,226 A | 7/1989 | Julian et al. |
| 4,851,229 A | 7/1989 | Magruder et al. |
| 4,863,742 A | 9/1989 | Panoz et al. |
| 4,871,549 A | 10/1989 | Ueda et al. |
| 4,874,613 A | 10/1989 | Hsiao |
| 4,886,669 A | 12/1989 | Ventouras |
| 4,892,741 A | 1/1990 | Ohm et al. |
| 4,894,240 A | 1/1990 | Geoghegan et al. |
| 4,898,737 A | 2/1990 | Panoz et al. .................... 424/468 |
| 4,915,949 A | 4/1990 | Wong et al. |
| 4,938,968 A | 7/1990 | Mehta |
| 4,946,684 A | 8/1990 | Blank et al. |
| 4,957,745 A | 9/1990 | Jonsson et al. |
| 4,968,508 A | 11/1990 | Oren et al. |
| 4,971,805 A | 11/1990 | Kitanishi et al. |
| 4,983,401 A | 1/1991 | Eichel et al. |
| 5,006,345 A | 4/1991 | Lang |
| 5,011,692 A | 4/1991 | Fujioka et al. |
| 5,013,557 A | 5/1991 | Tai |
| 5,013,743 A | 5/1991 | Iwahi et al. |
| 5,017,122 A | 5/1991 | Staniforth |
| 5,017,381 A | 5/1991 | Maruyama et al. |
| 5,026,559 A | 6/1991 | Eichel et al. .................... 424/458 |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bucheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A * | 11/1993 | Chen .................... 424/451 |
| 5,275,827 A | 1/1994 | Spinelli et al. |
| 5,376,384 A | 12/1994 | Eichel et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A | 12/1995 | Eichel et al. |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chauveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A | 10/2000 | Grimmett et al. |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1 | 4/2002 | Khankari et al. |
| 6,368,625 B1 | 4/2002 | Siebert et al. |
| 6,368,628 B1 | 4/2002 | Seth |

(56) References Cited

U.S. PATENT DOCUMENTS

| | | |
|---|---|---|
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Chittamuru et al. |
| 6,432,534 B1 | 8/2002 | Hayakawa et al. |
| 6,465,009 B1 | 10/2002 | Liu et al. |
| 6,465,010 B1 | 10/2002 | Lagoviyer et al. |
| 6,495,160 B2 | 12/2002 | Esposito et al. |
| 6,500,454 B1 | 12/2002 | Percel et al. |
| 6,509,036 B2 | 1/2003 | Pather et al. |
| 6,531,152 B1 | 3/2003 | Lerner et al. |
| 6,551,617 B1 | 4/2003 | Corbo et al. |
| 6,579,535 B2 | 6/2003 | Valentine et al. |
| 6,596,311 B1 | 7/2003 | Dobetti |
| 6,602,521 B1 | 8/2003 | Ting et al. |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 | 12/2003 | Percel et al. |
| 6,663,893 B2 | 12/2003 | Corbo et al. |
| 6,740,341 B1 | 5/2004 | Holt et al. |
| 6,897,205 B2 | 5/2005 | Beckert et al. |
| 7,048,945 B2 | 5/2006 | Percel et al. |
| 2001/0007680 A1 | 7/2001 | Kolter et al. |
| 2001/0014340 A1 | 8/2001 | Ohta et al. |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1 | 12/2002 | Cade et al. |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 | 8/2003 | Percel et al. |
| 2003/0161888 A1 | 8/2003 | Fernandez et al. |
| 2003/0215500 A1 | 11/2003 | Ohta et al. |
| 2004/0047906 A1 | 3/2004 | Percel et al. |
| 2004/0121010 A1 | 6/2004 | Hirsh et al. |
| 2004/0122106 A1 | 6/2004 | Ohta et al. |
| 2004/0126427 A1 | 7/2004 | Venkatesh et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Brushci et al. |
| 2006/0057199 A1 | 3/2006 | Venkatesh et al. |
| 2006/0078614 A1 | 4/2006 | Venkatesh et al. |
| 2006/0105038 A1 | 5/2006 | Lai et al. |
| 2006/0105039 A1 | 5/2006 | Lai et al. |
| 2006/0246134 A1 | 11/2006 | Venkatesh |
| 2009/0263480 A1 | 10/2009 | Lai et al. |

FOREIGN PATENT DOCUMENTS

| | | |
|---|---|---|
| EP | 0239361 A1 | 9/1987 |
| EP | 0349103 A1 | 1/1990 |
| EP | 0357369 A2 | 3/1990 |
| EP | 0391518 A2 | 10/1990 |
| EP | 0431877 A1 | 6/1991 |
| EP | 0516345 A1 | 12/1992 |
| EP | 0538034 A1 | 4/1993 |
| EP | 0553777 A2 | 8/1993 |
| EP | 0650826 A1 | 5/1995 |
| EP | 0721777 A2 | 7/1996 |
| EP | 0815931 A1 | 1/1998 |
| EP | 0294493 A1 | 12/1998 |
| EP | 0914818 A1 | 5/1999 |
| EP | 0914823 A1 | 5/1999 |
| EP | 1010423 A2 | 6/2000 |
| EP | 0582396 B1 | 1/2001 |
| EP | 1070497 A1 | 1/2001 |
| EP | 1072257 A1 | 1/2001 |
| EP | 1157690 A1 | 11/2001 |
| EP | 1156786 BI | 3/2003 |
| EP | 1366759 A1 | 12/2003 |
| EP | 0914823 B1 | 12/2004 |
| EP | 2319498 A1 | 5/2011 |
| FR | 2679451 A1 | 1/1993 |
| FR | 2766089 A1 | 1/1999 |
| FR | 2778848 A1 | 11/1999 |
| GB | 2053787 A | 2/1981 |
| GB | 8824392 | 9/1989 |
| GB | 2224207 A | 5/1990 |
| JP | 49-69819 | 7/1974 |
| JP | 55-129224 A | 10/1980 |
| JP | 56-014098 A | 10/1981 |
| JP | 61-143316 A | 7/1986 |
| JP | 62-50445 B2 | 10/1987 |
| JP | 62-242616 A | 10/1987 |
| JP | 62-246513 A | 10/1987 |
| JP | 62-252723 A | 11/1987 |
| JP | 63-162619 A | 7/1988 |
| JP | 63-270624 A | 11/1988 |
| JP | 1-503385 A | 11/1989 |
| JP | 1-313420 A | 12/1989 |
| JP | 2-500747 A | 3/1990 |
| JP | 2-164824 A | 6/1990 |
| JP | 2-172918 A | 7/1990 |
| JP | 2-289512 A | 11/1990 |
| JP | 3-240724 A | 10/1991 |
| JP | 5-271054 A | 10/1993 |
| JP | 5-310558 A | 11/1993 |
| JP | 6-53658 B2 | 7/1994 |
| JP | 6-321790 A | 11/1994 |
| JP | 7-69889 A | 3/1995 |
| JP | 7-124231 A | 5/1995 |
| JP | 8-503482 A | 4/1996 |
| JP | 8-175978 A | 7/1996 |
| NZ | 550608 A | 11/2005 |
| NZ | 554346 A | 5/2006 |
| WO | WO 88/08703 A1 | 11/1988 |
| WO | WO 88/08704 A2 | 11/1988 |
| WO | WO 92/10173 A1 | 6/1992 |
| WO | WO 93/00097 A1 | 1/1993 |
| WO | WO 93/12769 A1 | 7/1993 |
| WO | WO 93/13758 A1 | 7/1993 |
| WO | WO 93/15724 A1 | 8/1993 |
| WO | WO 94/08576 A1 | 4/1994 |
| WO | WO 94/12180 A1 | 6/1994 |
| WO | WO 97/41878 A1 | 11/1997 |
| WO | WO 97/47287 A1 | 12/1997 |
| WO | WO 99/04763 A1 | 2/1999 |
| WO | WO 00/25752 A1 | 5/2000 |
| WO | WO 00/33821 A1 | 6/2000 |
| WO | WO 00/42998 A1 | 7/2000 |
| WO | WO 00/51568 A1 | 9/2000 |
| WO | WO 00/59486 A2 | 10/2000 |
| WO | WO 01/13898 A2 | 3/2001 |
| WO | WO 01/72285 A1 | 10/2001 |
| WO | WO 01/80829 A2 | 11/2001 |
| WO | WO 02/13794 A1 | 2/2002 |
| WO | WO 02/43704 A2 | 6/2002 |
| WO | WO 02/057475 A1 | 7/2002 |
| WO | WO 02/085336 A1 | 10/2002 |
| WO | WO 03/013492 A1 | 2/2003 |
| WO | WO 03/039520 A1 | 3/2003 |
| WO | WO 03/026613 A1 | 4/2003 |
| WO | WO 03/041683 A2 | 5/2003 |
| WO | WO 03/047552 A2 | 6/2003 |
| WO | WO 2004/009058 A1 | 1/2004 |
| WO | WO 2004/022037 A1 | 3/2004 |
| WO | WO 2004/087111 A1 | 10/2004 |
| WO | WO 2005/097064 A2 | 10/2005 |
| WO | WO 2005/105049 A2 | 11/2005 |

OTHER PUBLICATIONS

Albrecht, "International Search Report," 6 pages, from International Patent Appl. No. PCT/US02/31535, European Patent Office (Feb. 3, 2003).

(56) References Cited

OTHER PUBLICATIONS

Anwar et al., "Chronotherapeutics for Cardiovascular Disease," Drugs 55(5):631-643 (1998).
Bauer et al., Pharmarzeutische Technologie, 5th Edition, 1997, Govi Verlag Frankfurt, pp. 164-166.
Berigan, "Atomoxetine Used Adjunctively With Selective Serotonin Reuptake Inhibitors to Treat Depression," Prim. Care. Companion J. Clin. Psychiatry 6(2):93-94 (2004).
Bodmeier et al., "Theophylline Tablets Coated with Aqueous Latexes Containing Dispersed Pore Formers," J. Pharm. Sci. 79(10):925-928 (1990).
Database WPI, Section Ch, Week 198748, Derwent Publications, Ltd., London, GB; AN 1987-338131, XP002156870, OPD date Apr. 14, 1986.
Fell, Letter to the Editor, J. Pharm. Pharmacol. 1968, vol. 20, pp. 657-658.
FMC Corporation Product Specification for Avicel PH, 2005.
Foreign non-patent publication from Japanese textbook, 1989, Hirokawa Publishing Co.
Foreign non-patent publication Sysmex No. FP3OSCJ001, Original doc 2008.
Fubara, "International Preliminary Examination Report," 3 pages, from International Patent Appl. No. PCT/US02/31535, European Patent Office (Jun. 19, 2003).
Gordon et al., "Effect of the Mode of Super Disintegrant Incorporation on Dissolution in Wet Granulated Tables," J. Pharm. Sci. 82:220-226 (1993).
Gorman et al., An Evaluation of Croscarmellose as a Tablet Disintegrant in Direct Compression Systems, Drug. Dev. Ind. Pharm. 1982; vol. 8, pp. 397-410.
Handbook (Binran) of Granule, vol. 1, Ohmsha Ltd., p. 434 & 438 (May 3, 1975).
Ishino et al., "Design and Preparation of Pulsatile Release Tablet as a New Oral Drug Delivery System," Chem. Pharm. Bull. 40(11):3036-3041 (1992).
Kaneto et al., 2000, Latest Pharmacy, Hirokawa Publishing Co., 1 Edition.
Kawashima, "Low-Substituted Hydroxypropylcellulose as a Sustained-Drug Release Matrix Base or Disintegrant Depending on Its Particle Size and Loading in Formulation," Pharm. Res. 1993, vol. 10(3), pp. 351-355.
Kornblum, "A New Tablet Disintegrating Agent," J. Pharm. Sci., Jan. 1973, vol. 62(1), pp. 43-49.
Kratochvil et al., "Atomoxetine: a selective noradrenaline reuptake inhibitor for the treatment of attention-deficit/hyperactivity disorder," Exp. Opin. Pharmacother. 4(7):1165-1174 (2003).
McKenna et al., "Effect of particle size on the compaction mechanism and tensile strength of tablets," J. Pharm. Pharmacol. Jun. 1982, vol. 34(6), pp. 347-351.
McKetta et al., "Table of Contents," Encyclopedia of Chemical Processing and Design (1989), p. xi, xii.
McKetta et al., Encyclopedia of Chemical Processing and Design, "Organic Phase Separation Conservation," p. 167 (1989).
Mitsuo et al., Pharmaceutics Manual, 1989, Pharmaceutics Manual, Nanzando Co. Ltd.
Nwokole et al., "Tolerance during 29 days of conventional dosing with cimetidine, mizatidine, famotidine or ranitidine," Aliment. Pharmacol. Ther. 4(Suppl. 1):29-45 (1990) Abstract only.
Oh, "International Preliminary Report on Patentability," 5 pages, from International Appl. No. PCT/US2005/037084, United States Patent and Trademark Office, Alexandria, Virginia, USA (mailed Aug. 24, 2007).
Ohira et al., "Effects of Various Histamine $H_2$-Receptor Antagonists on Gastrointestinal Motility Translation and Gastric Emptying," J. Smooth Muscle Res. 29:131-142 (1993) with translation.
Pharmaceutical Excipients. London: Pharmaceutical Press. Electronic Version, 2006, Mannitol., Accessed Jan. 3, 2006.
Pharmaceutical Excipients. London: Pharmaceutical Press. Electronic Version, 2006, Lactose Monohydrate, Accessed Jan. 3, 2006.
Pharmaceutical Excipients. London: Pharmaceutical Press. Electronic Version, 2006, Croscarmellose sodium, Accessed Jan. 3, 2006.
Rankin, "International Search Report," 6 pages, PCT International Application No. PCT/US02/39238, European Patent Office (May 8, 2003).
Rudnic et al., "Some Effects of Relatively Low Levels of Eight Tablet Disintegrants on a Direct Compression System," Drug. Dev. Ind. Pharm. 1981, vol. 7(3), pp. 347-358.
Rudnic et al., "Studies of the Utility of Cross Linked Polyvinlpolypyrrolidine as a Tablet Disintegrant," Drug Development and Industrial Pharmacy, 1980, vol. 6, No. 3, pp. 291-309.
Sato et al., "Anticonvulsant effects of tigabine, a new antiepileptic drug: the profile of action in the rat kindling model of epilepsy," Epilepsia 37(Supp. 3):110-111 (1996).
Schifferer, "International Search Report," 4 pages, from International Appl. No. PCT/US2005/037084, European Patent Office, Rijswijk, The Netherlands (mailed Jun. 1, 2006).
Schifferer, "Written Opinion of the International Search Authority," 6 pages, from International Appl. No. PCT/US2005/037084, European Patent Office, Munich, Germany (mailed Jun. 1, 2006).
Shangraw et al., "A new era of tablet disintegrants," Pharm. Technol. 1980, vol. 4(10), pp. 49-57.
Tirkkonen and Paronen, "Enhancement of drug release from ethylcellulose microcapsules using solid sodium chloride in the wall," Int. J. Pharmaceutics 88:39-51 (1992).
Trottier and Wood, 2005, "Particle Size Measurement," Kirk-Othmer Encyclopedia of Chemical Technology (Extract of 1. Introduction; 2. Data Representation; 4. Measurement Methods; 8. Selection of Equipment).
Ueki et al., "Nizatidine Comparably Enhances Postprandial Gastric Motility to Existing Gastroprokinetics in Dogs," Jpn. Pharmacol. Ther. 28(11):925-930 (2000).
Uhl, "International Search Report," 5 pages, International Patent Appl. No. PCT/US2006/016538, European Patent Office (Feb. 27, 2007).
Uhl, "Written Opinion of the International Searching Authority," 6 pages, International Patent Appl. No. PCT/US2006/016538, European Patent Office (Feb. 27, 2007).
van Kamp et al., "Improvement by super disintegrants of the properties of tablets containing lactose, prepared by wet granulation," Pharmaceutisch Weekblad Scientific Edition; 1983, vol. 5, pp. 165-171.
Villa, "International Search Report," 4 pages, from International Appl. No. PCT/US2005/038328, European Patent Office, Rijswijk, The Netherlands (mailed Sep. 15, 2006).
Villa, "Written Opinion of the International Search Authority," 5 pages, from International Appl. No. PCT/US2005/038328, European Patent Office, Munich, Germany (mailed Sep. 15, 2006).
Vromans et al., "Studies on tableting properties of lactose," Pharmaceutisch Weekblad Scientific Edition; 1985, vol. 7, pp. 186-193.
Yamahara et al., "Effect of release rate on bioavailability of control-release multiple unit dosage forms," Yakuzaigaku 55(2):99-107 (1995).
Yamamoto et al., "The Effects of Nizatidine on the Function of Esophageal Motility in Patients with Gastroesophageal Reflux Disease (GERD)," Jpn. Pharmacol. Ther. 28(5):419-424 (2000).
Young, "International Preliminary Examination Report" 6 pages, PCT International Application No. PCT/US02/39238, United States Patent and Trademark Office (Apr. 27, 2005).
Young, "Written Opinion," 5 pages, PCT International Application No. PCT/US02/39238, United States Patent and Trademark Office (Jan. 13, 2005).
Zheng et al., "Influence of Eudragit® NE 30 D Blended with Eudragit® L 30 D-55 on the Release of Phenylpropanolamine Hydrochloride from Coated Pellets," Drug Development and Industrial Pharmacy 29(3):357-366 (2003).
Zimmer, "European Search Report," 3 pages, European patent appl. No. 01103129.1, European Patent Office (Jun. 9, 2001).
Zimmer, "International Search Report," 4 pages, PCT International Application No. PCT/US01/04012, European Patent Office (Jun. 19, 2001).

* cited by examiner

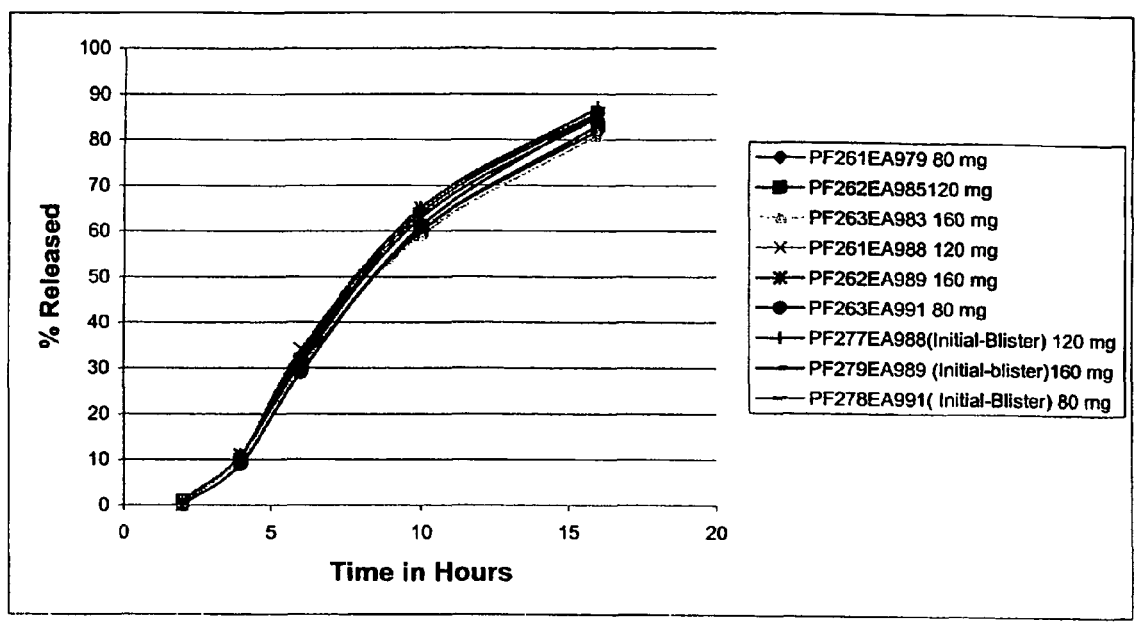
Figure 1: Propranolol HCl TSR Formulations (Capsules): Release Profiles for Pilot and Pivotal Clinical Supplies Figure 2: Mean Propranolol Concentration Versus Time Plots Following a Single Dose of TSR Formulation (Capsules)
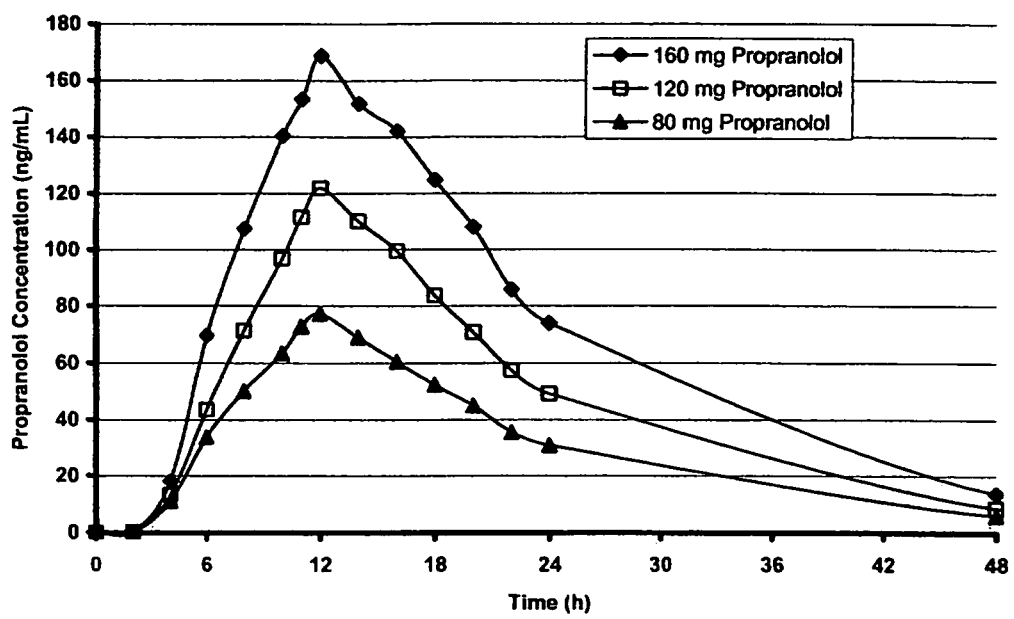

Mean Plasma Propranolol Profiles from TSR Formulation 160 mg vs. Inderal® LA 160 mg
Figure 3(a): Single Dose Administration
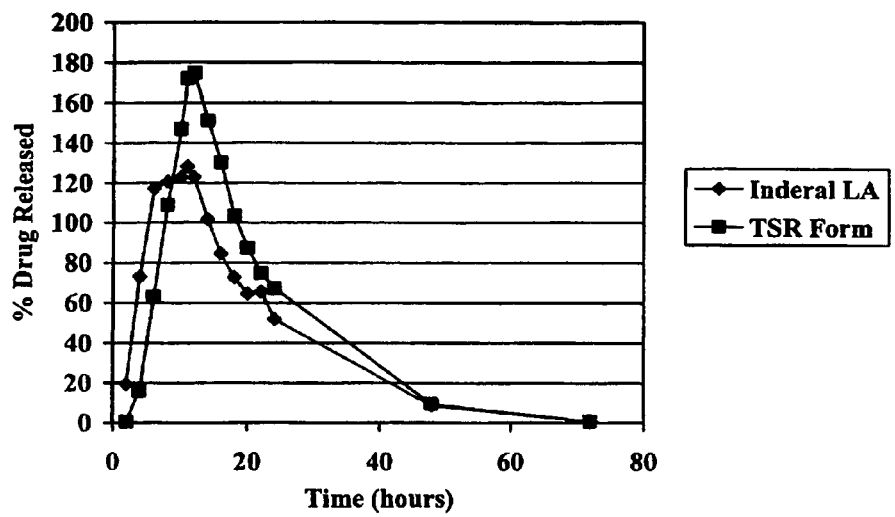
Figure 3(b): Steady State
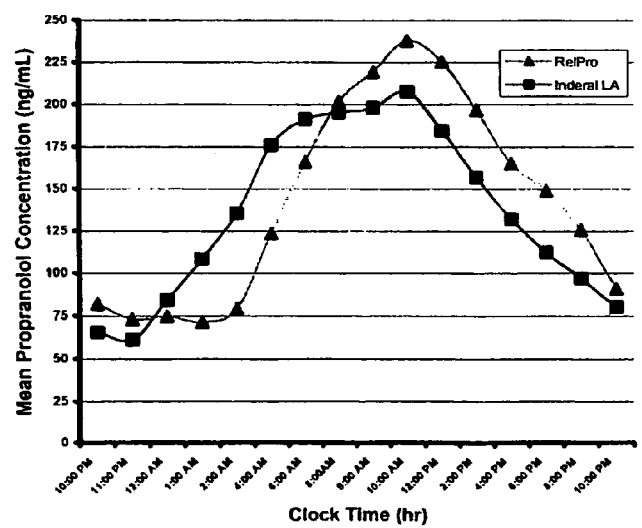

TIMED, SUSTAINED RELEASE SYSTEMS FOR PROPRANOLOL

RELATED APPLICATIONS

This application is a continuation of U.S. application Ser. No. 10/453,848 filed Jun. 2, 2003, which is a continuation-in-part application of U.S. application Ser. No. 10/334,052 filed Dec. 30, 2002, abandoned, which is a continuation of U.S. application Ser. No. 09/971,167 filed Oct. 4, 2001, now U.S. Pat. No. 6,500,454. Each of the foregoing applications, each document cited or referenced in each of the foregoing applications and during prosecution of each of the foregoing applications ("application cited documents"), each document referenced or cited in each of the application cited documents, each documents cited or referenced in this application ("herein cited documents") and each document cited or referenced in each of the herein cited documents are all incorporated herein by reference in their entireties.

TECHNICAL FIELD

A major objective of chronotherapy for cardiovascular diseases is to deliver the drug in higher concentrations during the time of greatest need, typically during the early morning hours, and in lesser concentrations when the need is less, such as during the late evening and early sleep hours. This can be accomplished by administration of the release dosage form of the present invention, which relates to a controlled absorption of propranolol from dosage forms. The release dosage form of the present invention, which relates to a controlled absorption of propranolol from dosage form, comprises an assembly of Timed, Sustained Release (TSR) Beads, each of which is designed to release as a sustained release pulse after a predetermined delay ("time-controlled" drug delivery instead of "rate-controlled") with resulting plasma concentration(s) of propranolol varying in a circadian rhythm fashion following administration of a single dosage form at bedtime, thereby minimizing potential risks of a cardiovascular disease, such as stroke, heart attack and myocardial infarction, decreasing systolic blood pressure, or reducing hypertension or beta-adrenergic stimulation, treating cardiac arrhythmia, hypertrophic subaortic stenosis or angina, or preventing migraine and thus enhancing patient compliance and therapeutic efficacy, while reducing cost of treatment.

BACKGROUND OF THE INVENTION

Many therapeutic agents are most effective when made available at a constant rate at or near the absorption site. The absorption of therapeutic agents thus made available generally results in desired plasma concentrations leading to maximum efficacy and minimum toxic side effects. Much effort has been devoted to developing sophisticated drug delivery systems, such as osmotic devices, for oral application. However, there are instances where maintaining a constant blood level of a drug is not desirable. For example, a "position-controlled" drug delivery system (e.g., treatment of colon disease or use of colon as an absorption site for peptide and protein based products) may prove to be more efficacious. A pulsatile delivery system is capable of providing one or more immediate release pulses at predetermined time points after a controlled lag time or at specific sites. However, there are only a few such orally applicable pulsatile release systems due to the potential limitation of the size or materials used for dosage forms. Ishino et al. disclose a dry-coated tablet form in Chemical Pharm. Bull. Vol. 40 (11), 3036-041 (1992). U.S. Pat. No. 4,851,229 to Magruder et al., U.S. Pat. No. 5,011,692 to Fujioka et al., U.S. Pat. No. 5,017,381 to Maruyama et al., U.S. Pat. No. 5,229,135 to Philippon et al., and U.S. Pat. No. 5,840,329 to Bai disclose preparation of pulsatile release systems. Some other devices are disclosed in U.S. Pat. No. 4,871,549 to Ueda et al. and U.S. Pat. Nos. 5,260,068; 5,260,069; and 5,508,040 to Chen. U.S. Pat. Nos. 5,229,135 and 5,567,441 both to Chen disclose a pulsatile release system consisting of pellets coated with delayed release or water insoluble polymeric membranes incorporating hydrophobic water insoluble agents or enteric polymers to alter membrane permeability. U.S. Pat. No. 5,837,284 to Mehta et al. discloses a dosage form which provides an immediate release dose of methylphenidate upon oral administration, followed by one or more additional doses spread over several hours.

There is a well-established circadian variation in frequency of onset of cardiovascular events including ventricular arrhythmias, stroke, angina, and myocardial infarction. The peak frequency of such events is exhibited in the morning hours, theoretically in conjunction with the morning surge in systolic blood pressure and heart rate. There is also some evidence of a secondary peak in frequency of such events in the late afternoon or evening hours. Although there is some evidence which suggests that long acting propranolol may blunt the circadian variability of sudden cardiac death, it does not appear to attenuate early morning increases in blood pressure observed in hypertensive patients. Thus it would be physiologically advantageous to tailor plasma concentrations of propranolol to the typical circadian patterns of blood pressure and heart rate.

Chronotherapeutics is a means of proportioning plasma drug concentrations during a 24-hour period, relative to the biological rhythm determinates of disease activity. The objective of chronotherapy is to deliver the drug in higher concentrations during the time of greatest need, and in lesser concentrations when the need is less. The dosage forms disclosed in the prior arts above are not specifically designed to provide drug release profiles varying predictably in time over 24 hours, i.e., in a circadian rhythm fashion to effectively treat cardiovascular diseases. The dosage forms of the present invention, Propranolol Hydrochloride ER Capsules, 80, 120, and 160 mg), which are typically administered at bedtime, i.e., at about 10:00 PM, are novel formulations designed to provide reductions in blood pressure and heart rate over 24 hours, including optimal protection in the early morning hours when patients are most vulnerable to cardiovascular events. At steady state, blood levels of propranolol begin to increase approximately 4 hours after bedtime administration of these capsules and rise progressively over the early morning hours to reach peak plasma concentrations approximately 14 hours after dosing. These capsules produce peak plasma propranolol levels that rise slowly to attenuate the rapid increase in blood pressure and heart rate that precedes and follows waking. This increase is associated with circadian variation in catecholamine secretion and in rennin release. The rise in plasma propranolol concentration after dosing with these capsules parallel the circadian rise in morning blood pressure associated with target organ damage in patients with hypertensive and ischemic cardiovascular disease.

Propranolol [1-(isopropyl amino)-3-(1-naphthyloxy)-2-propanol] is a beta-adrenergic blocking agent and as such is a competitive inhibitor of the effects of catecholamines at beta-adrenergic receptor sites. The principal effect of propranolol is to reduce cardiac activity by diminishing or preventing beta-adrenergic stimulation. By reducing the rate and force of contraction of the heart, and decreasing the rate of conduction of impulses through the conducting system, the response of the heart to stress and exercise is reduced. These properties are used in the treatment of angina in an effort to reduce the oxygen consumption and increase the exercise tolerance of the heart. Propranolol is also used in the treatment of cardiac arrhythmias to block adrenergic stimulation of cardiac pacemaker potentials. Propranolol is also beneficial in the long term treatment of hypertension. Other uses of propranolol are in the treatment of migraine and anxiety.

SUMMARY OF THE INVENTION

The preparation of the dosage form of the present invention is fully described in U.S. Pat. No. 6,500,454 assigned to Eurand Pharmaceuticals, Ltd., which is incorporated here by reference in its entirety. The dosage form, a hard gelatin capsule, is a timed, sustained release multi-particulate dosage form comprising a propranolol core having a first membrane of a sustained release polymer and a second membrane of a mixture of water insoluble polymer and an enteric polymer ($2^{nd}$ or outer coating), wherein the water insoluble polymer and the enteric polymer may be present at a weight ratio of from 10:1 to 1:2, and the total weight of the coatings is 10 to 60 weight % based on the total weight of the coated beads. In some cases depending on the type of drug release profile needed, an immediate release component may be included to provide a modified, timed, sustained release dosage form. When administered at bedtime, the dosage form comprising Timed, Sustained Release Capsule, commercially known as TSR Formulation XL, is designed to provide reductions in blood pressure and heart rate over 24 hours, including optimal protection in the early morning hours when patients are most vulnerable to cardiovascular events. At steady state, blood levels of propranolol begin to increase approximately 4 hours after bedtime administration of TSR Formulation XL and rise progressively over the early morning hours to reach peak plasma concentrations approximately 14 hours after dosing. TSR Formulation XL produces peak plasma propranolol levels that rise slowly to attenuate the rapid increase in blood pressure and heart rate that precedes and follows waking. This increase is associated with circadian variation in catecholamine secretion and in rennin release. The rise in plasma propranolol concentration after dosing with TSR Formulation XL parallels the circadian rise in morning blood pressure associated with target organ damage in patients with hypertensive and ischemic cardiovascular disease.

BRIEF DESCRIPTION OF THE FIGURES

The invention will be described in further detail with reference to the accompanying Figures wherein:

FIG. 1 shows in vitro drug release profiles from Propranolol HCl TSR Capsules, 80, 120, and 160 mg, used in the pivotal clinical studies.

FIG. 2 shows mean propranolol concentration versus time plots for 80 mg, 120 mg and 160 mg dosage strengths of TSR Formulation following a single administration of the drug product.

FIG. 3*a* shows the mean propranolol plasma concentration over time following a single dose of 160 mg propranolol TSR Formulation or 160 mg Inderal™ LA.

FIG. 3*b* shows the mean propranolol plasma concentration over time during multiple dosing of either Inderal® LA 160 mg or TSR Formulation 160 mg (i.e., at steady state).

DETAILED DESCRIPTION OF THE INVENTION

The active core of the novel dosage form of the present invention may comprise an inert particle or an acidic or alkaline buffer crystal, which is coated with a propranolol-containing film-forming formulation and preferably a water-soluble film forming composition to form a water-soluble/dispersible particle. Alternatively, the active core may be prepared by granulating and milling and/or by extrusion and spheronization of a polymer composition containing propranolol. Generally, the individual polymeric coating on the active core will be from 1 to 50% based on the weight of the coated particle. Those skilled in the art will be able to select an appropriate amount of propranolol for coating onto or incorporating into the core to achieve the desired dosage. In one embodiment, the inactive core may be a sugar sphere, a buffer crystal or an encapsulated buffer crystal, such as calcium carbonate, sodium bicarbonate, fumaric acid, tartaric acid, etc. Buffer crystals are useful to alter the microenvironment.

In accordance with one embodiment of the present invention, the water soluble/dispersible drug-containing particle is first coated with a water insoluble polymer ($1^{st}$ or inner coating), and further coated with a mixture of a water insoluble polymer and an enteric polymer ($2^{nd}$ or outer coating). The water insoluble polymer and enteric polymer may be present at a weight ratio of from 10:1 to 1:2, more preferably 2:1 to 1:1, and the total weight of the coatings is 10 to 60 weight % based on the total weight of the coated beads. The polymeric coatings typically contain plasticizers and may be applied from aqueous and/or solvent based systems.

The composition of the outer layer and the individual weights of the inner and outer layers of the polymeric membrane are optimized for achieving desired drug release profiles. The unit dosage form according to certain embodiments of the present invention may comprise an immediate release bead population which provides an immediate release component of propranolol to act as a bolus dose.

The invention also provides a method of making a timed, sustained release dosage form comprising the steps of:

1. preparing an active-containing core by coating an inert particle such as a non-pareil seed, an acidic buffer crystal or an alkaline buffer crystal, with propranolol and polymeric binder or by granulation and milling or by extrusion/spheronization to form an immediate release (IR) bead;

2. coating the core with a plasticized solution or suspension of a water insoluble polymer to form sustained release (SR) coated drug particle;

3. coating the SR coated particle with a mixture of plasticized water insoluble and enteric polymers to form a Timed Sustained Release (TSR) coated drug particle; and filling capsules with TSR particles to produce Timed, Sustained Release (TSR) capsules.

The release profile for TSR beads can be determined according to the following procedure:

Dissolution testing is conducted with a USP Apparatus 2 (Paddles at 50 rpm) using a two-stage dissolution medium (first 2 hours in 700 mL 0.1N HCl at 37° C. followed by dissolution at pH=6.8 obtained by the addition of 200 mL of pH modifier). Drug release with time is determined by HPLC on samples pulled at selected intervals.

The TSR Beads prepared in accordance with present invention release not more than 20%, more preferably not more than 10%, and most preferably not more than 5% in 2 hours, about 5-35%, more preferably about 5-25%, and most preferably about 5-15% in 4 hours, about 10-60%, more preferably about 20-45%, and most preferably about 25-35% in 6 hours, about 40-90%, more preferably about 50-80%, and most preferably about 55-70% in 10 hours, and not less than 60%, more preferably not less than 70%, and most preferably not less than 75% in 16 hours.

In accordance with the present invention, the desired release properties are obtained as a result of the different characteristics of the two coating layers. The inner layer membrane provides sustained or extended drug release over several hours, while the second or outer membrane provides a lag time of three to four hours. Typical release profiles for SR beads (ethylcellulose coated drug particle) and TSR beads when tested by the two-stage dissolution medium are provided in Table 1, below:

TABLE 1

| Time | SR Beads (% Propranolol Released) | TSR Beads |
|---|---|---|
| 1 hr | 11.2 | 0.0 |
| 2 hr | 32.1 | 0.1 |
| 3 hr | 39.8 | 1.1 |
| 4 hr | 52.3 | 8.6 |
| 5 hr | 62.3 | 18.3 |
| 6 hr | 69.2 | 27.4 |
| 8 hr | 79.4 | 44.5 |
| 10 hr | 84.6 | 58.4 |
| 12 hr | 90.0 | 68.8 |
| 16 hr | 95.6 | 90.0 |

It is also possible that the TSR Capsule may optionally also contain a population of Immediate Release (IR) beads or particles to provide an immediate release component of active to act as a bolus dose in addition to the timed, sustained release of active provided by the TSR beads. These dosage forms provide a Modified Timed Sustained Release (MTSR) profile.

An aqueous or a pharmaceutically acceptable solvent medium may be used for preparing drug containing core particles. The type of film forming binder that is used to bind propranolol to the inert sugar sphere is not critical but usually water-soluble, alcohol-soluble or acetone/water soluble binders are used. Binders such as polyvinylpyrrolidone (PVP), polyethylene oxide, hydroxypropyl methylcellulose (HPMC), hydroxypropylcellulose (HPC), polysaccharides, such as dextran, and corn starch may be used at concentrations of from about 0.5 to 10 weight %. Propranolol may be present in the coating formulation in solution form or may be suspended at a solids content up to about 35 weight % depending on the viscosity of the coating formulation.

Dissolution rate controlling polymers suitable for incorporating in the formulation for producing granules by high shear or fluid bed granulation or by dry granulation include high molecular weight hydroxypropyl methylcellulose, hydroxypropyl cellulose, ethyl cellulose, sodium carboxymethyl cellulose, alginic acid, polymethylmethacrylate copolymers and polyvinyl acetate/crotonic acid copolymer or combinations thereof. Acidic buffers, which help maintain an acidic microenvironment within drug containing particles, include fumaric acid, tartaric acid, maleic acid, succinic acid and mixtures thereof. An acidic microenvironment helps dissolve basic drugs with poor solubility at the intestinal pHs and become available for absorption. Examples of alkaline buffers include sodium bicarbonate, calcium carbonate, and sodium dihydrogen phosphate.

Propranolol, a binder such as PVP, a buffer, a dissolution rate controlling polymer (if used), and optionally other pharmaceutically acceptable excipients are blended together in a high shear granulator such as Fielder or a fluid bed granulator such as Glatt GPCG 5 and granulated to form agglomerates by adding/spraying a granulating fluid such as water or alcohol and dried. The wet mass can be extruded and spheronized to produce spherical particles (beads) using an extruder/marumerizer. In these embodiments, the drug load could be as high as 90% by weight based on the total weight of the extruded/spheronized core. The blend can also be used to produce dry granules by slugging in a tablet press or a chilsonator, without the addition of any granulating fluid.

The active containing cores (beads, pellets or granular particles) thus obtained may be coated with one or two layers of polymers to obtain desired release profiles with or without a lag time. The inner layer membrane, which largely controls the rate of release following imbibition of water or body fluids into the core, comprises a water insoluble polymer, such as ethylcellulose, at a thickness of from 1 weight % up to 6 weight %, preferably from 1.5 to 4% and most preferably about 2%, depending on the solvent or latex suspension based coating formulation used.

The outer membrane, which largely controls the lag time of up to 6 hours, comprises an enteric polymer and a water insoluble polymer at a thickness of 10 to 60, preferably from 10 to 56 weight % based on the total weight of the coated beads. The ratio of water insoluble polymer to enteric polymer may vary from 10:1 to 1:2, preferably from 2:1 to 1:1.

Representative examples of water insoluble polymers useful in the invention include cellulose derivatives (e.g. ethylcellulose), polyvinyl acetate (Kollicoat SR30D from BASF), neutral copolymers based on ethyl acrylate and methylmethacrylate, copolymers of acrylic and methacrylic acid esters with quaternary ammonium groups, such as Eudragit NE, RS or RS30D, RL or RL30D and the like.

Representative examples of enteric polymers useful in the invention include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methamethacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rhom Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Both enteric and water insoluble polymers used in forming the membranes are usually plasticized. Representative examples of plasticizers that may be used to plasticize the membranes include triacetin, tributyl citrate, triethyl citrate, acetyl tri-n-butyl citrate diethyl phthalate, castor oil, dibutyl sebacate, acetylated monoglycerides and the like or mixtures thereof. The plasticizer may comprise about 3 to 30 wt. % and more typically about 10 to 25 wt. % based on the polymer. The type of plasticizer and its content depends on the polymer or polymers, nature of the coating system (e.g., aqueous or solvent based, solution or dispersion based and the total solids).

In general, it is desirable to prime the surface of the particle before applying the pulsatile release membrane coatings or to separate the different membrane layers by applying a thin hydroxypropyl methylcellulose (HPMC) (Opadry Clear) film. While HPMC is typically used, other primers such as hydroxypropylcellulose (HPC) can also be used.

The membrane coatings can be applied to the core using any of the coating techniques commonly used in the pharmaceutical industry, but fluid bed coating is particularly useful.

The present invention is applied to multi-dose forms, i.e., drug products in the form of multi-particulate dosage forms (pellets, beads, granules or mini-tablets) or in other forms suitable for oral administration The following non-limiting examples illustrate the capsule dosage forms manufactured in accordance with the invention, which exhibit in vitro drug release profiles, similar to that predicted by performing modeling exercises, and in vivo plasma concentrations following circadian rhythm pharmaco-dynamic profile of angina attacks. Such dosage forms when administered at bed time, would enable maintaining drug plasma concentration at a level potentially beneficial in minimizing the occurrence of heart attacks in the early hours of the morning.

EXAMPLES

Modified Timed, Sustained Release (MTSR) capsules of Propranolol Hydrochloride may contain a mixture of two sets of beads: The first set is referred to as immediate release (IR) Beads and are designed to provide a loading dose by releasing all of the drug within the first hour, preferably within the first 30 minutes. The second set is referred to as Timed Sustained Release (TSR) Beads and are designed to release the remainder of the dose slowly over a period of 12-15 hours after a 3-5-hour lag time. The TSR Beads are produced by applying an inner layer of sustained release coating (with a dissolution rate controlling polymer such as ethylcellulose) (producing IntR Beads, intermediate release beads) and then an outer layer of pulse coating (with a blend of an enteric polymer such as HPMCP and a water-insoluble polymer such as ethylcellulose) on IR Beads. The two sets of beads (IR and TSR) when filled into capsule shells at an appropriate ratio will produce the target circadian rhythm release profile required for maintaining drug plasma concentrations at potentially beneficial levels in minimizing the occurrence of heart attacks. Alternatively, the capsules may comprise only the TSR Beads, the capsules containing only the TSR Beads are referred to as TSR Formulation. It is well known that the blood pressure begins to drop as the night advances, and consequently, only the Formulations containing only the TSR beads for oral administration are described below.

Example 1

Propranolol HCl (45.2 kg) was slowly added to an aqueous solution of polyvinylpyrrolidone (2.34 kg Povidone K-30) and mixed well. #25-30 mesh sugar spheres (31.6 kg) were coated with the drug solution in a Glatt fluid bed granulator. The drug containing pellets were dried, and a seal coat of Opadry Clear (2% w/w) was first applied (batch size: 80.75 kg). The inner sustained release coating was applied to the active particles (73.7 kg) by spraying a solution of ethylcellulose and diethyl phthalate in 98/2 acetone/water. The outer coating of a blend of ethylcellulose and HPMCP plasticized with diethyl phthalate was sprayed onto the active particles having the inner coating to produce TSR Beads (batch size: 82.5 kg). These TSR Beads were filled into hard gelatin capsules using an MG capsule filling equipment to produce Propranolol hydrochloride TSR Capsules, 80, 120, and 160 mg.

These Propranolol TSR Capsules were tested for drug release profiles by the two-stage dissolution method, wherein capsules were dissoluted at pH 1.5 in 700 ml 0.1N HCl for two hours followed by testing at pH 6.8 in 900 mL obtained by adding 200 mL of concentrated buffer modifier. FIG. 1 presents the drug release profiles from Propranolol Hydrochloride TSR Capsules, 80, 120, and 160 mg, used in the pivotal clinical studies.

Example 2

A double-blind, randomized, placebo-controlled, 4-period crossover study to assess the efficacy and dose proportionality of TSR Formulation 80 mg, 120 mg, and 160 mg in 39 healthy male and female subjects of ages 18 to 40 was carried out. In each study period a single dose of one strength of TSR Formulation or placebo was administered at approximately 10:00 PM. There was a minimum of 7 days between the administration of each dose of TSR Formulation or placebo. Efficacy was assessed by the mean change in post-exercise heart rate, heart rate pressure product, and systolic blood pressure from pre-dose to Hour 24 post-dose (trough) assessments. The secondary efficacy variable was the mean change in post-exercise heart rate from pre-dose to Hour 12. Post-exercise heart rate was used as a surrogate marker for anti-anginal efficacy.

Analyses for concentrations of total plasma propranolol (conjugated and unconjugated) on the blood samples collected were carried out using a validated high performance liquid chromatography (HPLC) method. Plasma samples were collected pre-dose and up to 72 hours post-dose. The limit of quantitation was 2 ng/mL. FIG. 2 displays mean propranolol concentration versus time plots for 80 mg, 120 mg and 160 mg dosage strengths of TSR Formulation following a single administration of the drug product. Maximum plasma propranolol concentrations ($C_{max}$) occurred at about 12 hours post-dose for the 80 mg, 120 mg, and 160 mg dose groups. After 12 hours post-dose, plasma propranolol concentrations decreased at a consistent and similar rate in all dose groups. The absorption lag time ($T_{lag}$) and time to maximum drug concentration ($T_{max}$) were similar across all TSR Formulation dose groups. Table 2 summarizes the pharmacokinetic parameters for this study.

TABLE 2

Summary of Pharmacokinetic Parameters - Pharmacokinetic Population

| Parameter/Statistic | TSR Formulation | | |
|---|---|---|---|
| | 80 mg (N = 36) | 120 mg (N = 36) | 160 mg (N = 36) |
| $AUC_{(0-T)}$ (ng · hr/mL)$^a$ | | | |
| N | 36 | 36 | 36 |
| Mean | 1442.6 | 2270.1 | 3417.1 |
| SD | 844.19 | 1230.62 | 2047.40 |
| Median | 1220.8 | 2102.2 | 3047.2 |
| Minimum | 551.8 | 594.3 | 1211.1 |
| Maximum | 3792.1 | 5928.7 | 11596.2 |
| $AUC_{(0-\infty)}$ (ng · hr/mL) | | | |
| N | 36 | 36 | 36 |
| Mean | 1568.5 | 2412.6 | 3589.0 |
| SD | 865.20 | 1287.41 | 2080.77 |
| Median | 1422.9 | 2180.1 | 3199.5 |
| Minimum | 605.1 | 646.6 | 1291.1 |
| Maximum | 3994.0 | 6660.0 | 12157.2 |
| $C_{max}$ (ng/mL) | | | |
| N | 36 | 36 | 36 |
| Mean | 80.5 | 130.0 | 177.2 |
| SD | 31.53 | 52.30 | 70.62 |
| Median | 75.8 | 117.0 | 171.0 |
| Minimum | 30.1 | 41.5 | 72.4 |
| Maximum | 155.0 | 249.0 | 426.0 |
| $t_{1/2}$ (hr) | | | |
| N | 36 | 36 | 36 |
| Mean | 9.5 | 8.5 | 9.1 |
| SD | 5.05 | 4.7 | 4.35 |
| Median | 8.1 | 7.1 | 8.8 |
| Minimum | 3.3 | 3.2 | 2.8 |
| Maximum | 22.7 | 20.2 | 21.3 |

TABLE 2-continued

Summary of Pharmacokinetic Parameters - Pharmacokinetic Population

| Parameter/Statistic | TSR Formulation | | |
|---|---|---|---|
| | 80 mg (N = 36) | 120 mg (N = 36) | 160 mg (N = 36) |
| $T_{max}$ (hr) | | | |
| N | 36 | 36 | 36 |
| Mean | 12.2 | 12.8 | 12.8 |
| SD | 1.93 | 2.46 | 2.72 |
| Median | 12.0 | 12.0 | 12.0 |
| Minimum | 8.0 | 10.0 | 8.0 |
| Maximum | 20.0 | 20.0 | 24.0 |
| $T_{lag}$ (hr) | | | |
| N | 36 | 36 | 36 |
| Mean | 2.2 | 2.1 | 1.9 |
| SD | 1.05 | 0.89 | 0.67 |
| Median | 2.0 | 2.0 | 2.0 |
| Minimum | 0.0 | 0.0 | 0.0 |
| Maximum | 4.0 | 4.0 | 4.0 |
| $K_{el}$ (1/hr) | | | |
| N | 36 | 36 | 36 |
| Mean | 0.0965 | 0.1076 | 0.0958 |
| SD | 0.05090 | 0.05384 | 0.05125 |
| Median | 0.0862 | 0.0987 | 0.0788 |
| Minimum | 0.0305 | 0.0343 | 0.0326 |
| Maximum | 0.2107 | 0.2193 | 0.2517 |

[a]t is the last time point with measurable propranolol concentration

Linear regression analyses on untransformed pharmacokinetic parameters showed dose proportionality and a linear dose-response relationship between the TSR Formulation dosage strengths and the pharmacokinetic parameters $AUC_{0-T}$ (area under the concentration-time curve to the last measurable time point calculated by the linear trapezoidal rule), $AUC_{0-\infty}$ (are under the concentration-time curve to infinity), and $C_{max}$. Results of linear regression and ANOVA after log-transformation and dose-normalization confirmed a dose proportional relationship between $AUC_{0-T}$, $AUC_{0-\infty}$, and $C_{max}$ and TSR Formulation 80 mg, 120 mg, and 160 mg doses.

Regarding efficacy, maximum decreases in systolic blood pressure were noted at 8-10 hours post-dose in all treatment groups. Maximum decreases in diastolic blood pressure were noted at 8-10 hours post-dose in the TSR Formulation 120 mg and placebo groups and at 14 hours post-dose in the TSR Formulation 80 mg and 160 mg groups. Maximum decreases in heart rate were observed at 10 hours post-dose in all treatment groups. Mean changes in systolic and diastolic blood pressure and heart rate showed increases from pre-dose values at 72 hours post-dose in all treatment groups. No subject experienced postural hypotension during the study.

Only the TSR Formulation 80 mg dose group showed a statistically significant decrease in the adjusted mean change in exercise-induced heart rate from baseline at 24 hours post-dose, relative to placebo (primary end point) and in 12-hour post-exercise heart rate (secondary end point). No dose response was observed for heart rate. Statistically significant changes, relative to placebo, were observed for two primary end points: hour 24 heart rate-pressure product seen for the lowest and highest doses and hour 24 heart rate at the lowest dose of TSR Formulation; these data support the efficacy of TSR formulations in the prevention and treatment of angina. Demonstration of blunting of exercise response to beta blockade for the 12-hour post p.m. dosing exercise challenge also supports the efficacy of the TSR Formulation in protection against morning ischemic events.

Example 3

A randomized, open-label, two-period crossover study to evaluate the single and multiple dose bioavailability and safety of TSR Formulation 160 mg compared to Inderal® LA 160 mg capsules was carried out. The primary objective of this study was to evaluate the relative bioavailability of TSR Formulation 160 mg to Inderal® LA 160 mg as assessed by an ANOVA on AUCs after single and multiple dose administrations. The secondary objective was to explore the pharmacokinetics of TSR Formulation and Inderal® LA after single and multiple dose administrations. Safety and tolerability were measured by evaluating adverse events, laboratory values, physical examinations, electrocardiograms, and vital signs.

Subjects were healthy, adult, males between 18 and 45 years of age who met the study eligibility criteria. In Period 1 of the study, following a 4-hour fasting period on Day 1, subjects received a single dose of the study drug (TSR Formulation or Inderal® LA) between 9:30 and 10:30 PM. Serial blood samples for plasma total propranolol determinations were collected for 72 hours. Subjects received a daily dose of their Period 1 drug on Days 4 to 8 and 24-hour trough blood samples were collected. A seven-day washout period followed, and the same procedures were followed for Period 2 with the other study drug as determined by the sequence to which the subjects were randomized. Analyses for concentrations of total plasma propranolol (conjugated and unconjugated) on the blood samples collected were carried out using a validated high performance liquid chromatography (HPLC) method. The limit of quantitation was 2 ng/mL.

Plots of the mean propranolol plasma concentration over time following a single dose of 160 mg propranolol TSR Formulation or 160 mg Inderal® LA are presented in FIG. 3a. Following a single dose of TSR Formulation 160 mg there was a delayed release of propranolol for 2 to 4 hours, whereas release of propranolol following a single dose of Inderal® LA 160 mg was almost immediate. Within 3 hours after administration of Inderal® LA, mean plasma propranolol concentrations increased to approximately 50% of the mean maximum propranolol concentration. In contrast, following administration of TSR Formulation, 50% of the mean maximum plasma propranolol concentration was not reached until approximately 7 hours post administration. Between 10 hr and 12 hr post dose, mean plasma concentrations in the Inderal® LA group remained relatively constant (range 122.8 ng/mL to 128.2 ng/mL) while mean plasma concentrations in the TSR Formulation group steadily increased (range 146.9 ng/mL to 174.8 ng/mL). The time to maximum plasma levels of propranolol ($T_{max}$) was 10.5 hr and 11.9 hr for subjects administered Inderal® LA and TSR Formulation, respectively. The $C_{max}$ values were 149.1 ng/mL for Inderal® LA and 186.5 ng/mL for TSR Formulation, respectively. At 24 hr post-dose, the mean plasma concentrations were 51.8 ng/mL and 67.3 ng/mL in the Inderal® LA and TSR Formulation groups, respectively. After 24 hr post-dose, plasma concentrations decreased at a consistent and similar rate in both groups. The elimination half-life ($t_{1/2}$) was similar for both formulations.

A summary of the single dose pharmacokinetic parameters of $AUC_{0-T}$, $AUC_{0-\infty}$ and $C_{max}$ following an Analysis of Variance (ANOVA) is given in Table 3. The adjusted mean $C_{max}$ values were 131.0 ng/mL and 171.3 ng/mL for subjects administered Inderal® LA and TSR Formulation, respectively.

TABLE 3

Summary of Analysis of Variance on Single Dose Pharmacokinetic Parameters

| Parameter/Statistic[1] | Inderal ® LA 160 mg (N = 35) | TSR Formulation 160 mg (N = 35) | Ratio (TSR Formulation/Inderal ® LA) (N = 35) |
|---|---|---|---|
| $AUC_{0-T}$ (ng · hr/mL) | | | |
| Adjusted Mean | 2588.7 | 2943.9 | 1.1 |
| 90% CI | (2399.77, 2792.44) | (2729.06, 3175.62) | (1.02, 1.27) |
| $AUC_{0-\infty}$ (ng · hr/mL) | | | |
| Adjusted Mean | 2604.8 | 2962.7 | 1.1 |
| 90% CI | (2415.90, 2808.43) | (2747.90, 3194.37) | (1.02, 1.27) |
| $C_{max}$ (ng/mL) | | | |
| Adjusted Mean | 131.0 | 171.3 | 1.3 |
| 90% CI | (117.52, 146.12) | (153.66, 191.04) | (1.12, 1.53) |

[1]Adjusted mean and 90% CI calculated from ANOVA on log-transformed parameter with subject, period, sequence, and treatment as fixed effects. Adjusted means and CIs displayed have been transformed from the log to the arithmetic scale.
CI: Confidence Interval FIG. 3b displays the mean propranolol plasma concentration over time during multiple dosing of either Inderal® LA 160 mg or TSR Formulation 160 mg (i.e., at steady state). Following multiple doses of TSR Formulation 160 mg, there was a delayed release of propranolol for 2 to 6 hours, whereas the release of propranolol for Inderal® LA occurred after a slight delay of less than 1 hour. At steady state, the mean maximum plasma propranolol concentrations ($C_{max\,SS}$) were 229.9 ng/mL and 248.3 ng/mL for subjects administered Inderal® LA and TSR Formulation, respectively. Mean minimum plasma propranolol concentrations ($C_{min}$) at steady state were 56.3 ng/mL and 58.9 ng/mL for subjects administered Inderal® LA and TSR Formulation, respectively. The mean time to observed maximum propranolol concentration at steady state ($T_{max\,SS}$) was approximately 2 hours greater for TSR Formulation (12.6 hr) than for Inderal® LA (10.9 hr). Similarly, the mean time to the observed minimum plasma propranolol concentration at steady state ($T_{min}$) was approximately 2 hours greater for TSR Formulation (7.3 hr) than for Inderal® LA (5.1 hr). Steady state plasma propranolol concentrations for both TSR Formulation and Inderal® LA were attained after 2 days of dosing during the multiple dosing period. Both formulations showed similar accumulation at steady state and propranolol concentrations fluctuated in a similar manner over the dosing interval.

Table 4 describes a summary of the results of the ANOVA performed on the pharmacokinetic parameters $AUC_{0-\tau SS}$, $C_{AV\,SS}$, $R_{ac\,SS}$, and $Fi_{SS}$.

TABLE 4

Summary of Analysis of Variance on Steady State Pharmacokinetic Parameters

| Parameter/Statistic[1] | Inderal ® LA 160 mg (N = 35) | Formulation TSR 160 mg (N = 35) | Ratio (Formulation TSR/Inderal ® LA) (N = 35) |
|---|---|---|---|
| $AUC_{0-\tau SS}$ (ng · hr/mL) | | | |
| Adjusted Mean | 3115.0 | 3325.6 | 1.1 |
| 90% CI | (2928.62, 3313.28) | (3126.56, 3537.22) | (.98, 1.16) |
| $C_{AV\,SS}$ (ng/mL) | | | |
| Adjusted Mean | 128.7 | 137.5 | 1.1 |
| 90% CI | (121.02, 136.92) | (129.22, 146.20) | (.98, 1.17) |
| $R_{ac\,SS}$ ($AUC_{0-\tau SS}$/$AUC_{0-\tau\,Day\,1}$) | | | |
| Adjusted Mean | 1.7 | 1.7 | 1.0 |
| 90% CI | (1.54, 1.94) | (1.47, 1.86) | (0.81, 1.13) |
| $Fi_{SS}$ ($C_{max}-C_{min}/C_{av}$) | | | |
| Adjusted Mean | 114.3 | 126.7 | 1.1 |
| 90% CI | (105.38, 123.93) | (116.87, 137.45) | (0.99, 1.24) |

[1]Adjusted mean and 90% CI calculated from ANOVA on log-transformed parameter with subject, period, sequence, and treatment as fixed effects. Adjusted means and CIs displayed have been transformed from the log to the arithmetic scale.
CI: Confidence Interval Example 4

A randomized, double-blind, parallel, placebo-controlled, multicenter trial to study the efficacy, safety and steady state pharmacokinetics of 80 mg, 120 mg, 160 mg, and 640 mg TSR Formulation in patients with essential hypertension was carried out. The primary objective of this study was to assess the efficacy of the TSR Formulation in subjects with essential hypertension by evaluating the mean change from Baseline to Week 8 in morning sitting diastolic pressure. Subjects were randomized to one of the five double-blind treatment groups: placebo, TSR Formulation 80 mg/day, TSR Formulation 120 mg/day, TSR Formulation 160 mg/day, and TSR Formulation 640 mg/day taken once daily before bedtime. During Week 1 and Week 2 subjects were up titrated to the appropriate dose for 6 weeks, and then they were down titrated for the last two weeks of the study.

Morning sitting diastolic pressure, the measure of primary efficacy, decreased from Baseline to Endpoint for the placebo and all four TSR Formulation groups. Statistically significant differences in the magnitude of the decrease between the placebo group and the 120 mg, 160 mg, and 640 mg TSR Formulation groups were observed. Statistical trends were observed for the 80 mg TSR Formulation dose group. These results demonstrate that the TSR Formulation, administered once daily at bedtime in dosage strengths of 80 mg to 640 mg propranolol is an effective antihypertensive agent.

What is claimed is:

1. A timed, sustained-release (TSR) pharmaceutical formulation comprising timed, sustained release beads, wherein said TSR beads comprise:
   a) a core comprising propranolol or a pharmaceutically acceptable salt thereof;
   b) a first membrane comprising a first water insoluble polymer surrounding said core;
   c) a second outer membrane comprising a mixture of a second water insoluble polymer and an enteric polymer;
   wherein said formulation provides a lag time in propranolol blood plasma concentration of about 2 to about 6 hours,
   wherein said formulation comprises about 80 mg, about 120 mg, or about 160 mg of propranolol or a pharmaceutically acceptable salt thereof,
   wherein said formulation provides a maximum blood plasma concentration ($C_{max}$) between about 10 and about 14 hours following administration.

2. The pharmaceutical formulation of claim 1, wherein the pharmaceutical formulation comprises about 160 mg of propranolol or a pharmaceutically acceptable salt thereof, and provides a maximum blood plasma concentration ($C_{max}$) within the range of 80% to 125% of about 177 ng/mL of propranolol between about 10 and about 14 hours following administration and an $AUC_{0-T}$ within the range of 80% to 125% of about 3417 ng·hr/mL.

3. The pharmaceutical formulation of claim 1, wherein the pharmaceutical formulation comprises about 120 mg of propranolol or a pharmaceutically acceptable salt thereof, and provides a maximum blood plasma concentration ($C_{max}$) within the range of 80% to 125% of about 130 ng/ml, of propranolol between about 10 and about 14 hours following administration and an $AUC_{0-T}$ within the range of 80% to 125% of about 2270 ng·hr/mL.

4. The pharmaceutical formulation of claim 1, wherein the pharmaceutical formulation comprises about 80 mg of propranolol or a pharmaceutically acceptable salt thereof, and provides a maximum blood plasma concentration ($C_{max}$) within the range of 80% to 125% of about 81 ng/mL of propranolol between about 10 and about 14 hours following administration and an $AUC_{0-T}$ within the range of 80% to 125% of about 1443 ng·hr/mL.

5. The pharmaceutical formulation of claim 1 wherein the first and second water insoluble polymers are independently selected from the group consisting of ethylcellulose, polyvinyl acetate, neutral copolymers based on ethyl acrylate and methylmethacrylate, and copolymers of acrylic and methacrylic acid esters with quaternary ammonium groups.

6. The pharmaceutical formulation of claim 1 wherein the enteric polymer is selected from the group consisting of cellulose acetate phthalate, hydroxypropyl methylcellulose phthalate, hydroxypropyl methylcellulose acetate succinate, polyvinyl acetate phthalate, pH-sensitive methacrylic acid-methamethacrylate copolymers and shellac.

7. The pharmaceutical formulation of claim 1 whereby the first and second water insoluble polymers are ethylcellulose and the enteric polymer is a pH sensitive methacrylic acid-methamethacrylate copolymer.

8. A method of propranolol therapy which comprises administering orally to a human in need thereof the pharmaceutical formulation of claim 1.

9. A method of propranolol therapy which comprises administering orally to a human in need thereof the pharmaceutical formulation of claim 2.

10. A method of propranolol therapy which comprises administering orally to a human in need thereof the pharmaceutical formulation of claim 3.

11. A method of propranolol therapy which comprises administering orally to a human in need thereof the pharmaceutical formulation of claim 4.

12. A method of decreasing blood pressure during the early waking hours comprising orally administering once daily before bedtime to a human in need thereof the pharmaceutical formulation of claim 1.

13. A method of decreasing blood pressure during the early waking hours comprising orally administering once daily before bedtime to a human in need thereof the pharmaceutical formulation of claim 2.

14. A method of decreasing blood pressure during the early waking hours comprising orally administering once daily before bedtime to a human in need thereof the pharmaceutical formulation of claim 3.

15. A method of decreasing blood pressure during the early waking hours comprising orally administering once daily before bedtime to a human in need thereof the pharmaceutical formulation of claim 4.

16. A method of preventing angina during the early waking hours comprising orally administering once daily before bedtime to a human in need thereof the pharmaceutical formulation of claim 1.

17. A method of preventing angina during the early waking hours comprising orally administering once daily before bed time to a human in need thereof the pharmaceutical formulation of claim 2.

18. A method of preventing angina during the early waking hours comprising orally administering once daily before bedtime to a human in need thereof the pharmaceutical formulation of claim 3.

19. A method of preventing angina during the early waking hours comprising orally administering once daily before bedtime to a human in need thereof the pharmaceutical formulation of claim 4.

* * * * *